United States Patent
Rembiak et al.

(10) Patent No.: US 11,332,447 B2
(45) Date of Patent: May 17, 2022

(54) METHOD FOR PRODUCING HALOGENATED N-ARYLPYRAZOLES

(71) Applicant: Bayer Aktiengesellschaft, Leverkusen (DE)

(72) Inventors: Andreas Rembiak, Bad Soden (DE); Eike Kevin Heilmann, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 17/058,032

(22) PCT Filed: May 20, 2019

(86) PCT No.: PCT/EP2019/062924
§ 371 (c)(1),
(2) Date: Nov. 23, 2020

(87) PCT Pub. No.: WO2019/224139
PCT Pub. Date: Nov. 28, 2019

(65) Prior Publication Data
US 2021/0198209 A1 Jul. 1, 2021

(30) Foreign Application Priority Data
May 24, 2018 (EP) .................... 18174030

(51) Int. Cl.
*C07D 231/16* (2006.01)
(52) U.S. Cl.
CPC ............... *C07D 231/16* (2013.01)
(58) Field of Classification Search
CPC .................................................. C07D 231/16
USPC ..................................................... 548/377.1
See application file for complete search history.

(56) References Cited

U.S. PATENT DOCUMENTS

| | | | |
|---|---|---|---|
| 9,758,485 B2 | 9/2017 | Hallenbach | |
| 10,150,737 B2 | 12/2018 | Hallenbach | |
| 10,357,036 B2 | 7/2019 | Harsch | |
| 2011/0166143 A1 | 7/2011 | Bretschneider | |
| 2015/0322063 A1 | 11/2015 | Furuyama | |

FOREIGN PATENT DOCUMENTS

| | | |
|---|---|---|
| WO | 2008156739 A1 | 12/2008 |
| WO | 2015067646 A1 | 5/2015 |
| WO | 2015067647 A1 | 5/2015 |
| WO | 2016174052 A1 | 11/2016 |
| WO | 2017025590 A1 | 2/2017 |

OTHER PUBLICATIONS

Maes and Iskra, Eds., Topics in Heterocyclic Chem.: Halogenated Heterocycles (2012), 27(1-4) pp. 1-326.*
Mare et al., The Kinetics of Halogen Substitution, Part IV (1948) pp. 100-106.*
March, Adv. Org. Chem. 2nd. Ed. (1977), Halogen Electrophiles, pp. 482-483.*
Bovonsombat, P. et la. (2009). "Regioselective iodination of phenol and analogues using N-iodosuccinimide and p-toluenesulfonic acid," Tetrahedron Letters 50: 2664-2667.
Castanet, A.S. et al (2002). "Mild and regioselective iodination of electron-rich aromatics with N-iodosuccinimide and catalytic trifluoroacetic acid," Tetrahedron Letters 43: 5047-5048.
International Search Report dated Jul. 30, 2019 for PCT Application No. PCT/EP2019/062924, filed May 20, 2019, 7 pages.
Jiang, P.P. et al (2016). "A quick, mild and efficient bromination using a CFBSA/KBr system," RSC Adv. 6: 90031-90034.
Kim, M.M et al. (2008). "Green iodination of pyrazoles with iodine/hydrogen peroxide in water," Tetrahedron Letters 49: 4026-4028.
Lyalin, B.. et al. (Feb. 2014). "New approach to electrochemical iodination of arenes exemplified by the synthesis of 4iodopyrazoles of different structures," Russian Chemical Bulletin, International Edition, 63(2): 360-367.
Ruck, R.T. et al. (2012). "Route Development and Multikilogram GMP Delivery of a Somatostatin Receptor Antagonist," Org. Process Res. Dev. 16: 1329-1337.

* cited by examiner

*Primary Examiner* — Taofiq A Solola
(74) *Attorney, Agent, or Firm* — Morrison & Foerster LLP

(57) ABSTRACT

The present invention relates to a process for preparing compounds of the formula (I)

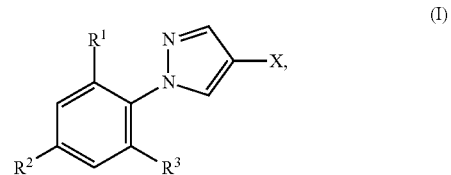

by halogenating compounds of the formula (II),

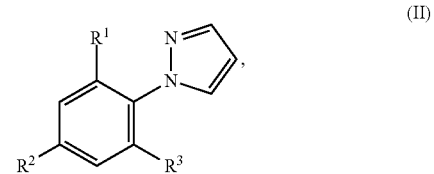

where in $R^1$, $R^2$, $R^3$ and X are defined according to the invention.

16 Claims, No Drawings

METHOD FOR PRODUCING HALOGENATED N-ARYLPYRAZOLES

CROSS REFERENCE TO RELATED APPLICATIONS

This application is a national stage application under 35 U.S.C. § 371 of International Application No. PCT/EP2019/062924, filed internationally on May 20, 2019, which claims the benefit of priority to European Application No. 18174030.9, filed May 24, 2018.

The present invention relates to a process for preparing compounds of the formula (I)

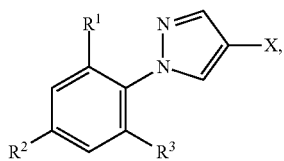

by halogenating compounds of the formula (II)

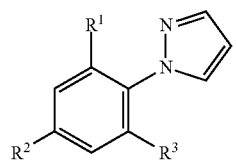

in which $R^1$, $R^2$, $R^3$ and X are defined as below.

Compounds of formula (I) and the preparation thereof have been described for example in WO2015/067646, WO2015/067647, WO2016/174052 and in WO2017/025590. However, disadvantages in the preparation processes described in these documents are the high reaction temperatures, the long reaction times in some cases, and the large fluctuations in the obtained yields of compounds of the general formula (I).

Alternative options that are generally known in the literature for halogenating pyrazoles describe the use of elemental iodine or bromine (WO 2008/156739) and also inorganic iodine and bromine salts (Russ. *Chem. Bull.* 2014, 63, 360, *RSC Advances* 2016, 6, 90031), optionally with addition of oxidizing compounds such as hydrogen peroxide (*Tetrahedron Lett.* 2008, 49, 4026) or cerium ammonium nitrate (US 2015/322063, US 2011/166143). Disadvantages in these processes are the need for elevated temperatures, at times incomplete or only low conversions to compounds of the general formula (I), the complex removal of heavy-metal salts and also the release of toxic and corrosive bromine or iodine vapours. For these reasons, these processes are unsuitable for industrial application.

Furthermore, the activation of organic, iodine-containing molecules for iodination by using strong acids has been described in the literature (*Tetrahedron Lett.* 2002, 43, 5047; *Tetrahedron Lett.* 2009, 50, 2664; *Org. Proc. Res. Dev.* 2012, 16, 1329). A disadvantage in these processes is the limitation to activated pyrazoles and aromatics in general and the use of relatively large catalytic or stoichiometric amounts of strong acids.

Halogenated N-arylpyrazole derivatives, however, are of great significance as a building block for synthesizing novel agrochemical active ingredients. The object of the present invention was therefore that of providing a process for preparing compounds of the general formula (I) which can be used industrially and cost-effectively and avoids the above-described disadvantages. It is also desirable to obtain the specific N-arylpyrazole derivatives with high yield and high purity, such that the target compound preferably does not have to be subjected to any further potentially complex purification.

This object was achieved according to the invention by a process for preparing compounds of the formula (I)

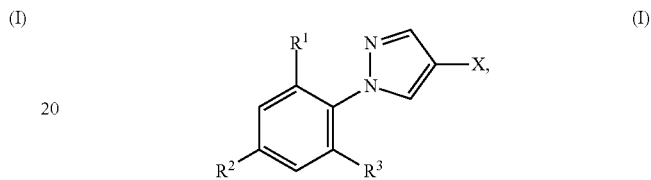

in which
X is halogen;
$R^1$ is hydrogen, cyano, halogen, $C_1$-$C_4$-alkyl optionally substituted by halogen or CN, or $C_1$-$C_4$-alkoxy optionally substituted by halogen,
$R^2$ is halogen, trifluoromethylsulfonyl, trifluoromethylsulfinyl, trifluoromethylsulfanyl, $C_1$-$C_4$-alkyl optionally substituted by halogen, or $C_1$-$C_4$-alkoxy optionally substituted by halogen and
$R^3$ is hydrogen, cyano, halogen, $C_1$-$C_4$-alkyl optionally substituted by halogen or CN, or $C_1$-$C_4$-alkoxy optionally substituted by halogen,
by halogenating compounds of the formula (II)

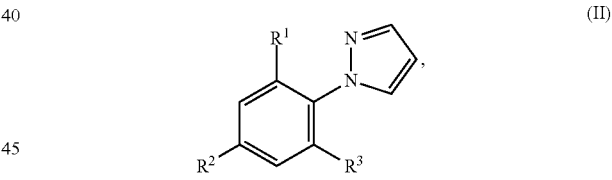

in which $R^1$, $R^2$ and $R^3$ are as defined above,
with an organic halogenating compound with addition of ≥0.0001 equivalent and <0.3 equivalent, based on the total molar amount of compound of the formula (II) used, of at least one acid selected from mineral acids, sulfonic acids, carboxylic acids and Lewis acids.

It has surprisingly now been found that the process according to the invention, via the addition of small catalytic amounts of an acid, leads to rapid halogenation with a constant, very good yield of compounds of the general formula (I) even at low temperatures. In addition, the process according to the invention permits a dose-controlled reaction regime and leads at the same time to an improvement in process reliability.

The preferred embodiments described below refer, if applicable, to all formulae described herein.

In one preferred embodiment of the invention,
$R^2$ is halogen-substituted $C_1$-$C_4$-alkyl or halogen-substituted $C_1$-$C_4$-alkoxy, such as for example difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, nonafluoro-sec-butyl, nonafluoro-tert-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy or pentafluoroethoxy.

Particularly preferably, $R^2$ is fluorine-substituted $C_1$-$C_4$-alkyl or fluorine-substituted $C_1$-$C_4$-alkoxy.

Very particularly preferably, $R^2$ is perfluoro-$C_1$-$C_3$-alkyl ($CF_3$, $C_2F_5$ or $C_3F7$ (n- or isopropyl)) or perfluoro-$C_1$-$C_3$-alkoxy ($OCF_3$, $OC_2F_5$ or $OC_3F_7$ (n- or isopropoxy)).

Especially preferably, $R^2$ is perfluoro-$C_1$-$C_3$-alkyl, such as trifluoromethyl, pentafluoroethyl, heptafluoroisopropyl or heptafluoro-n-propyl, especially heptafluoroisopropyl.

In one further preferred embodiment, $R^1$ and $R^3$ in each case independently of one another are a substituent selected from hydrogen, Cl, Br, F, $C_1$-$C_3$-alkyl, halogen-substituted $C_1$-$C_3$-alkyl, $C_1$-$C_3$-alkoxy or halogen-substituted $C_1$-$C_3$-alkoxy.

In one further preferred embodiment, $R^1$ and $R^3$ are the substituents described herein, but $R^1$ and $R^3$ are not simultaneously hydrogen in any compound.

In other words, when $R^1$ in a compound is hydrogen, $R^3$ is one of the other substituents described herein, and vice versa.

In one particularly preferred embodiment, $R^1$ and $R^3$ in each case independently of one another are Cl, Br, $C_1$-$C_3$-alkyl, or fluorine-substituted $C_1$-$C_3$-alkyl, $C_1$-$C_3$-alkoxy or fluorine-substituted $C_1$-$C_3$-alkoxy, especially Cl, Br, methyl, trifluoromethyl, trifluoromethoxy or difluoromethoxy.

In one very particularly preferred embodiment, $R^1$ and $R^3$ independently of one another are Cl, Br or F, especially Cl or Br. In one particularly advantageous configuration of the invention, $R^1$ and $R^3$ are the same halogen, especially chlorine.

In one preferred configuration of the invention, at least one of the radicals $R^1$, $R^2$, $R^3$ is halogen-substituted $C_1$-$C_4$-alkyl or halogen-substituted $C_1$-$C_4$-alkoxy, particularly preferably fluorine-substituted $C_1$-$C_3$-alkyl or fluorine-substituted $C_1$-$C_3$-alkoxy.

In one further particularly advantageous configuration of the invention, $R^1$ is halogen or $C_1$-$C_3$-alkyl, especially Br, Cl or methyl, $R^2$ is fluorine-substituted $C_1$-$C_4$-alkyl or fluorine-substituted $C_1$-$C_4$-alkoxy, especially heptafluoroisopropyl, and $R^3$ is halogen, $C_1$-$C_3$-alkyl or fluorine-substituted $C_1$-$C_3$-alkyl, $C_1$-$C_3$-alkoxy or fluorine-substituted $C_1$-$C_3$-alkoxy, especially Cl, methyl, trifluoromethyl, trifluoromethoxy or difluoromethoxy.

In one preferred configuration of the invention, X is chlorine, bromine or iodine, particularly preferably bromine or iodine and very particularly preferably iodine.

The pyrazoles of the formula (II) used as starting materials may for example be prepared from the corresponding hydrazine derivatives in analogy to the method described in WO2015/067646, WO2015/067647 and WO2016/174052.

Pyrazoles of the formula (II) that are preferably used are
1-[4-(1,1,1,2,3,3,3-heptafluoropropan-2-yl)-2,6-dimethylphenyl]-1H-pyrazole
1-[2,6-dichloro-4-(1,1,1,2,3,3,3-heptafluoropropan-2-yl)phenyl]-1H-pyrazole
1-[2-chloro-4-(1,1,1,2,3,3,3-heptafluoropropan-2-yl)-6-(trifluoromethyl)phenyl]-1H-pyrazole
1-[2-chloro-4-(1,1,1,2,3,3,3-heptafluoropropan-2-yl)-6-(trifluoromethoxy)phenyl]-1H-pyrazole
1-[2-chloro-6-(difluoromethoxy)-4-(1,1,1,2,3,3,3-heptafluoropropan-2-yl)phenyl]-1H-pyrazole
1-[4-(1,1,1,2,3,3,3-heptafluoropropan-2-yl)-2-methyl-6-(trifluoromethyl)phenyl]-1H-pyrazole
1-[2-bromo-4-(1,1,1,2,3,3,3-heptafluoropropan-2-yl)-6-(trifluoromethyl)phenyl]-1H-pyrazole
1-[2-bromo-4-(1,1,1,2,3,3,3-heptafluoropropan-2-yl)-6-(trifluoromethoxy)phenyl]-1H-pyrazole Particular preference is given here to:
1-[2,6-dichloro-4-(1,1,1,2,3,3,3-heptafluoropropan-2-yl)phenyl]-1H-pyrazole
1-[2-chloro-4-(1,1,1,2,3,3,3-heptafluoropropan-2-yl)-6-(trifluoromethyl)phenyl]-1H-pyrazole
1-[2-chloro-4-(1,1,1,2,3,3,3-heptafluoropropan-2-yl)-6-(trifluoromethoxy)phenyl]-1H-pyrazole
1-[2-chloro-6-(difluoromethoxy)-4-(1,1,1,2,3,3,3-heptafluoropropan-2-yl)phenyl]-1H-pyrazole
1-[2-bromo-4-(1,1,1,2,3,3,3-heptafluoropropan-2-yl)-6-(trifluoromethyl)phenyl]-1H-pyrazole
1-[2-bromo-4-(1,1,1,2,3,3,3-heptafluoropropan-2-yl)-6-(trifluoromethoxy)phenyl]-1H-pyrazole Very particular preference is given to 1-[2,6-dichloro-4-(1,1,1,2,3,3,3-heptafluoropropan-2-yl)phenyl]-1H-pyrazole.

The following preferred compounds of the formula (I) are correspondingly formed from these compounds:
4-bromo-1-[4-(1,1,1,2,3,3,3-heptafluoropropan-2-yl)-2,6-dimethylphenyl]-1H-pyrazole
4-bromo-1-[2,6-dichloro-4-(1,1,1,2,3,3,3-heptafluoropropan-2-yl)phenyl]-1H-pyrazole
4-bromo-1-[2-chloro-4-(1,1,1,2,3,3,3-heptafluoropropan-2-yl)-6-(trifluoromethyl)phenyl]-1H-pyrazole
4-bromo-1-[2-chloro-4-(1,1,1,2,3,3,3-heptafluoropropan-2-yl)-6-(trifluoromethoxy)phenyl]-1H-pyrazole
4-bromo-1-[2-chloro-6-(difluoromethoxy)-4-(1,1,1,2,3,3,3-heptafluoropropan-2-yl)phenyl]-1H-pyrazole
4-bromo-1-[4-(1,1,1,2,3,3,3-heptafluoropropan-2-yl)-2-methyl-6-(trifluoromethyl)phenyl]-1H-pyrazole
4-bromo-1-[2-bromo-4-(1,1,1,2,3,3,3-heptafluoropropan-2-yl)-6-(trifluoromethyl)phenyl]-1H-pyrazole
4-bromo-1-[2-bromo-4-(1,1,1,2,3,3,3-heptafluoropropan-2-yl)-6-(trifluoromethoxy)phenyl]-1H-pyrazole
1-[4-(1,1,1,2,3,3,3-heptafluoropropan-2-yl)-2,6-dimethylphenyl]-4-iodo-1H-pyrazole
1-[2,6-dichloro-4-(1,1,1,2,3,3,3-heptafluoropropan-2-yl)phenyl]-4-iodo-1H-pyrazole
1-[2-chloro-4-(1,1,1,2,3,3,3-heptafluoropropan-2-yl)-6-(trifluoromethyl)phenyl]-4-iodo-1H-pyrazole
1-[2-chloro-4-(1,1,1,2,3,3,3-heptafluoropropan-2-yl)-6-(trifluoromethoxy)phenyl]-4-iodo-1H-pyrazole
1-[2-chloro-6-(difluoromethoxy)-4-(1,1,1,2,3,3,3-heptafluoropropan-2-yl)phenyl]-4-iodo-1H-pyrazole
1-[4-(1,1,1,2,3,3,3-heptafluoropropan-2-yl)-2-methyl-6-(trifluoromethyl)phenyl]-4-iodo-1H-pyrazole
1-[2-bromo-4-(1,1,1,2,3,3,3-heptafluoropropan-2-yl)-6-(trifluoromethyl)phenyl]-4-iodo-1H-pyrazole
1-[2-bromo-4-(1,1,1,2,3,3,3-heptafluoropropan-2-yl)-6-(trifluoromethoxy)phenyl]-4-iodo-1H-pyrazole Particular preference is given here to
4-bromo-1-[2,6-dichloro-4-(1,1,1,2,3,3,3-heptafluoropropan-2-yl)phenyl]-1H-pyrazole 4-bromo-1-[2-chloro-4-(1,1,1,2,3,3,3-heptafluoropropan-2-yl)-6-(trifluoromethyl)phenyl]-1H-pyrazole
4-bromo-1-[2-chloro-4-(1,1,1,2,3,3,3-heptafluoropropan-2-yl)-6-(trifluoromethoxy)phenyl]-1H-pyrazole
4-bromo-1-[2-chloro-6-(difluoromethoxy)-4-(1,1,1,2,3,3,3-heptafluoropropan-2-yl)phenyl]-1H-pyrazole
4-bromo-1-[4-(1,1,1,2,3,3,3-heptafluoropropan-2-yl)-2-methyl-6-(trifluoromethyl)phenyl]-1H-pyrazole
4-bromo-1-[2-bromo-4-(1,1,1,2,3,3,3-heptafluoropropan-2-yl)-6-(trifluoromethyl)phenyl]-1H-pyrazole
4-bromo-1-[2-bromo-4-(1,1,1,2,3,3,3-heptafluoropropan-2-yl)-6-(trifluoromethoxy)phenyl]-1H-pyrazole
1-[2,6-dichloro-4-(1,1,1,2,3,3,3-heptafluoropropan-2-yl)phenyl]-4-iodo-1H-pyrazole
1-[2-chloro-4-(1,1,1,2,3,3,3-heptafluoropropan-2-yl)-6-(trifluoromethyl)phenyl]-4-iodo-1H-pyrazole
1-[2-chloro-4-(1,1,1,2,3,3,3-heptafluoropropan-2-yl)-6-(trifluoromethoxy)phenyl]-4-iodo-1H-pyrazole
1-[2-chloro-6-(difluoromethoxy)-4-(1,1,1,2,3,3,3-heptafluoropropan-2-yl)phenyl]-4-iodo-1H-pyrazole
1-[4-(1,1,1,2,3,3,3-heptafluoropropan-2-yl)-2-methyl-6-(trifluoromethyl)phenyl]-4-iodo-1H-pyrazole
1-[2-bromo-4-(1,1,1,2,3,3,3-heptafluoropropan-2-yl)-6-(trifluoromethyl)phenyl]-4-iodo-1H-pyrazole
1-[2-bromo-4-(1,1,1,2,3,3,3-heptafluoropropan-2-yl)-6-(trifluoromethoxy)phenyl]-4-iodo-1H-pyrazole Very particular preference is given to
1-[2,6-dichloro-4-(1,1,1,2,3,3,3-heptafluoropropan-2-yl)phenyl]-4-iodo-1H-pyrazole,
1-[2-chloro-4-(1,1,1,2,3,3,3-heptafluoropropan-2-yl)-6-(trifluoromethyl)phenyl]-4-iodo-1H-pyrazole,
1-[2-chloro-4-(1,1,1,2,3,3,3-heptafluoropropan-2-yl)-6-(trifluoromethoxy)phenyl]-4-iodo-1H-pyrazole and
1-[2-bromo-4-(1,1,1,2,3,3,3-heptafluoropropan-2-yl)-6-(trifluoromethoxy)phenyl]-4-iodo-1H-pyrazole.

In the context of the present invention, unless defined differently elsewhere, the term "alkyl", according to the invention either on its own or else in combination with further terms, for example haloalkyl, is understood to mean a radical of a saturated, aliphatic hydrocarbon group which has 1 to 12 carbon atoms, preferably has 1 to 6 and particularly preferably has 1 to 4 carbon atoms, and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl.

The term "alkoxy", either on its own or else in combination with further terms, for example haloalkoxy, is understood in the present case to mean an O-alkyl radical, where the term "alkyl" is as defined above.

According to the invention, unless defined differently elsewhere, the term "aryl" is understood to mean an aromatic radical having 6 to 14 carbon atoms, preferably phenyl, naphthyl, anthryl or phenanthrenyl, more preferably phenyl.

Halogen-substituted radicals, for example haloalkyl, are mono- or polyhalogenated up to the maximum possible number of substituents. In the case of polyhalogenation, the halogen atoms may be identical or different. Unless stated otherwise, optionally substituted radicals may be mono- or poly substituted, where the substituents in the case of polysubstitutions may be the same or different.

The ranges specified above generally or in preferred ranges apply correspondingly to the overall process. These definitions can be combined with one another as desired, i.e. including combinations between the respective preferred ranges.

Preference according to the invention is given to using processes in which there is a combination of the meanings and ranges specified above as being preferred.

Particular preference according to the invention is given to using processes in which there is a combination of the meanings and ranges specified above as being particularly preferred.

Very particular preference according to the invention is given to using processes in which there is a combination of the meanings and ranges specified above as being very particularly preferred.

Especially used according to the invention are processes in which there is a combination of the meanings and ranges specified above with the term "especially".

Specifically used according to the invention are processes in which there is a combination of the meanings and ranges specified above with the term "specifically".

Process Description
Preparation of Compounds of the Formula (I)

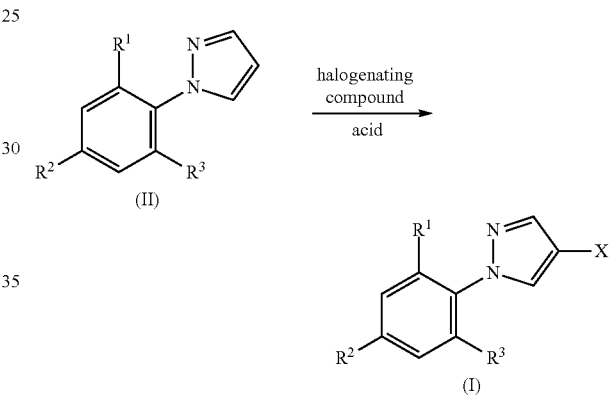

The radicals X, $R^1$, $R^2$ and $R^3$ have the meanings described above. The compounds of the structural formulae (I) and (II) are, for example, the compounds stated above as preferred pyrazoles and halopyrazoles.

The halopyrazoles of the general formula (I) are obtained with good yields and in high purity by the process according to the invention.

Inventive compounds of the general structure (I) are prepared by reacting the pyrazoles of the structure (II) with halogenating compounds with addition of ≥0.0001 equivalent and <0.3 equivalent, based on the total molar amount of compound (II) used, of at least one acid.

Suitable organic halogenating compounds are preferably selected from the N-halosuccinimides, especially from N-chlorosuccinimide (NCS), N-bromosuccinimide (NBS) or N-iodosuccinimide (NIS), the 1,3-dihalo-5,5-dimethylhydantoins, especially from 1,3-chloro-5,5-dimethylhydantoin (DCDMH), 1,3-dibromo-5,5-dimethylhydantoin (DBDMH) or 1,3-diiodo-5,5-dimethylhydantoin (DIDMH), or the halocyanuric acids, especially from 1,3,5-trichloro-1,3,5-triazine-2,4,6-trione, 1,3,5-tribromo-1,3,5-triazine-2,4,6-trione or 1,3-dibromo-1,3,5-triazine-2,4,6-trione. Particularly preferably, the halogenating compounds are selected from the N-halosuccinimides or 1,3-dihalo-5,5-dimethylhydantoins, very particular preference is given to 1,3-dihalo-5,5-dimethylhydantoins.

In addition, the halogenating compounds are particularly preferably selected from N-bromosuccinimide (NBS), N-iodosuccinimide (NIS), 1,3-dibromo-5,5-dimethylhydantoin (DBDMH), 1,3-diiodo-5,5-dimethylhydantoin (DIDMH), 1,3,5-tribromo-1,3,5-triazine-2,4,6-trione or 1,3-dibromo-1,3,5-triazine-2,4,6-trione, very particular preference is given to N-iodosuccinimide (NIS), 1,3-diiodo-5,5-dimethylhydantoin (DIDMH) or 1,3-dibromo-5,5-dimethylhydantoin (DBDMH) and specifically N-iodosuccinimide (NIS) and 1,3-diiodo-5,5-dimethylhydantoin (DIDMH).

The halogenating compounds may be used alone or in a combination of two or more, as long as the compounds used bear the same halogen.

The halogenating compound may be used according to the invention in a proportion of between 1.0 and 2.0 equivalents (monohalo compounds) or between 0.5 and 1.0 equivalent (dihalo compounds) and preferably between 1.1 and 1.2 equivalents (monohalo compounds) or between 0.55 and 0.8 equivalent (dihalo compounds), based on the total molar amount of compound (II) used.

The halogenating compound may be present according to the invention in pure form as a solid or as a suspension or solution in a suitable organic solvent which is inert under the reaction conditions, especially in the solvent previously selected for the reaction, preferably at a concentration of 40-90% by weight, particularly preferably at a concentration of 60-95% by weight. Suitable organic solvents are especially the solvents preferred for the overall process.

According to the invention, suitable acids are selected from mineral acids, sulfonic acids, carboxylic acids and Lewis acids.

According to the invention, the term "mineral acids" encompasses all inorganic acids not containing carbon, such as for example HF, HCl, HBr, HI, $H_2SO_4$, $HNO_3$, and $H_3PO_4$.

Suitable mineral acids are preferably selected from HCl, HF, $HNO_3$, $H_2SO_4$ and $H_3PO_4$, particularly preferably from $HNO_3$, HF and $H_2SO_4$, and $H_2SO_4$ is very particularly preferred.

According to the invention, the term "sulfonic acids" encompasses the optionally substituted arylsulfonic and alkylsulfonic acids generally known to those skilled in the art, such as for example methanesulfonic acid, trifluoromethanesulfonic acid, benzenesulfonic acid and p-toluenesulfonic acid.

Suitable sulfonic acids are preferably selected from methanesulfonic acid, trifluoromethanesulfonic acid, benzenesulfonic acid and para-toluenesulfonic acid, particularly preferably from methanesulfonic acid and para-toluenesulfonic acid, and methanesulfonic acid is very particularly preferred.

According to the invention, the term "carboxylic acids" encompasses all carbon-containing acids generally known to those skilled in the art and containing at least one carboxyl group (—COOH), such as for example optionally substituted alkylcarboxylic and arylcarboxylic acids and also optionally substituted alkyldicarboxylic and aryldicarboxylic acids.

Suitable carboxylic acids preferably have a pKa of ≤5, particularly preferably ≤3.

Suitable carboxylic acids are preferably selected from acetic acid, propionic acid, trifluoroacetic acid and trichloroacetic acid, particularly preferably from acetic acid, trifluoroacetic acid and trichloroacetic acid, and acetic acid or trifluoroacetic acid is very particularly preferred.

According to the invention, the term "Lewis acids" encompasses the inorganic and organic electrophilic electron pair acceptors generally known to those skilled in the art, especially anhydrous or hydrated inorganic salts of lithium or alkaline earth metals, especially Mg and Ca, for example as fluoride, chloride or bromide salts, nitrates, acetates, sulfates or trifluoromethanesulfonates (OTf), preferably as nitrates or trifluoromethanesulfonates (OTf), boron-group metals, especially Al, B or In, for example as fluoride, chloride or bromide salts, nitrates, acetates, sulfates or trifluoromethanesulfonates (OTf), preferably as fluoride, chloride or bromide salts, nitrates or trifluoromethanesulfonates (OTf), and of transition metals, especially Fe, Zn, Cu, Sc, Ti or Co, for example as fluoride, chloride, bromide salts, nitrates, acetates, sulfates or trifluoromethanesulfonates (OTf), preferably as nitrates or trifluoromethanesulfonates (OTf).

The salts can be used according to the invention in anhydrous form, but also in their hydrated form, especially with bound water of crystallization.

Although the use of other metal salts is possible from a technical point of view, it is not preferable from an economic and toxicological point of view.

Suitable Lewis acids are preferably anhydrous or hydrated salts selected from the fluoride, chloride or bromide salts, nitrates or trifluoromethanesulfonates (OTf) of the metals B or Al, from the nitrates or trifluoromethanesulfonates (OTf) of the alkaline earth metals Mg or the Ca or the nitrates or trifluoromethanesulfonates (OTf) of the transition metals Fe, Zn, Cu or Sc. The Lewis acids are particularly preferably anhydrous or hydrated salts selected from $Mg(NO_3)_2$, $Ca(NO_3)_2$, $Fe_2(NO_3)_3$, $Zn(NO_3)_2$, $Zn(OTf)_2$, $Cu(NO_3)_2$, $Sc(NO_3)_3$, $Ca(OTf)_2$, $Mg(OTf)_2$, $Cu(OTf)_2$, $BBr_3$, $BCl_3$, $BF_3*OEt_2$, $Al(NO_3)_3$, $Al(OTf)_3$, $Fe(OTf)_3$, $Cu(OTf)_2$ and $Sc(OTf)_3$, very particularly preferably from $Ca(OTf)_2$, $Mg(OTf)_2$, $Mg(NO_3)_2$, $Ca(NO_3)_2$, $Fe_2(NO_3)_3$ and $Fe(OTf)_3$.

According to the invention, suitable acids are preferably selected from HF, HCl, HBr, HI, $H_2SO_4$, $HNO_3$, and $H_3PO_4$, optionally substituted arylsulfonic and alkylsulfonic acids, optionally substituted alkylcarboxylic and arylcarboxylic acids, optionally substituted alkyldicarboxylic and aryldicarboxylic acids, where the carboxylic acids have a pKa of ≤5, and anhydrous or hydrated fluoride, chloride or bromide salts, nitrates, acetates, sulfates or trifluoromethanesulfonates (OTf) of lithium or of the alkaline earth metals, especially Mg and Ca, of the boron-group metals, especially Al, B or In, and of the transition metals, especially Fe, Zn, Cu, Sc, Ti or Co.

According to the invention, suitable acids are particularly preferably selected from HCl, HF, $HNO_3$, $H_2SO_4$, $H_3PO_4$, methanesulfonic acid, trifluoromethanesulfonic acid, benzenesulfonic acid, para-toluenesulfonic acid, acetic acid, propionic acid, trifluoroacetic acid, trichloroacetic acid and anhydrous or hydrated salts selected from the fluoride, chloride or bromide salts, nitrates or trifluoromethanesulfonates (OTf) of the metals B or Al, from the nitrates or trifluoromethanesulfonates (OTf) of the alkaline earth metals Mg or Ca, or nitrates or the trifluoromethanesulfonates (OTf) of the transition metals Fe, Zn, Cu or Sc.

According to the invention, suitable acids are very particularly preferably selected from $HNO_3$, HF, $H_2SO_4$, methanesulfonic acid, para-toluenesulfonic acid, acetic acid, trifluoroacetic acid, trichloroacetic acid, $Mg(NO_3)_2$, $Ca(NO_3)_2$, $Fe_2(NO_3)_3$, $Zn(NO_3)_2$, $Zn(OTf)_2$, $Cu(NO_3)_2$, $Sc(NO_3)_3$, $Ca(OTf)_2$, $Mg(OTf)_2$, $Cu(OTf)_2$, $BBr_3$, $BCl_3$, $BF_3*OEt_2$, $Al(NO_3)_3$, $Al(OTf)_3$, $Fe(OTf)_3$, $Cu(OTf)_2$ and $Sc(OTf)_3$.

According to the invention, suitable acids are specifically selected from $H_2SO_4$, methanesulfonic acid, acetic acid, trifluoroacetic acid, $Mg(NO_3)_2$, $Ca(NO_3)_2$, $Ca(OTf)_2$, $Mg(OTf)_2$, $Fe_2(NO_3)_3$ and $Fe(OTf)_3$.

Further preferred configurations of the process according to the invention concerning the acid used are detailed below.

According to the invention, the term "mineral acids" encompasses all inorganic acids not containing carbon, such as for example HF, HCl, HBr, HI, $H_2SO_4$, $HNO_3$, and $H_3PO_4$.

Suitable mineral acids are preferably selected from HCl, $H_2SO_4$ and $H_3PO_4$, particularly preferably from $H_2SO_4$ and $H_3PO_4$, and $H_2SO_4$ is very particularly preferred.

According to the invention, the term "sulfonic acids" encompasses the optionally substituted arylsulfonic and alkylsulfonic acids generally known to those skilled in the art, such as for example methanesulfonic acid, trifluoromethanesulfonic acid, benzenesulfonic acid and p-toluenesulfonic acid.

Suitable sulfonic acids are preferably selected from methanesulfonic acid, trifluoromethanesulfonic acid and para-toluenesulfonic acid, particularly preferably from methanesulfonic acid and trifluoromethanesulfonic acid, and methanesulfonic acid is very particularly preferred.

According to the invention, the term "carboxylic acids" encompasses all carbon-containing acids generally known to those skilled in the art and containing at least one carboxyl group (—COOH), such as for example optionally substituted alkylcarboxylic and arylcarboxylic acids and also optionally substituted alkyldicarboxylic and aryldicarboxylic acids.

Suitable carboxylic acids preferably have a pKa of ≤5, particularly preferably ≤3.

Suitable carboxylic acids are preferably selected from acetic acid, propionic acid, trifluoroacetic acid and trichloroacetic acid, particularly preferably from trifluoroacetic acid and trichloroacetic acid.

According to the invention, the term "Lewis acids" encompasses the inorganic and organic electrophilic electron pair acceptors generally known to those skilled in the art, such as for example anhydrous inorganic salts of lithium, alkaline earth metals (especially Mg and Ca), boron-group metals (especially Al, B or In) and transition metals (especially Fe, Zn, Cu, Sc, Ti or Co), for example as fluoride, chloride or bromide salts or trifluoromethanesulfonates (OTf). Although the use of other metal salts is possible from a technical point of view, it is not preferable from an economic and toxicological point of view.

Suitable Lewis acids are preferably selected from boron-group compounds, especially from $BBr_3$, $BCl_3$ and $BF_3*OEt_2$, from salts of the alkaline earth metals, especially $Mg(OTf)_2$ and $Ca(OTf)_2$, and the transition metal salts, especially $Zn(OTf)_2$, $Fe(OTf)_3$, $Cu(OTf)_2$, $Sc(OTf)_3$, particular preference is given to $Fe(OTf)_3$ and $Sc(OTF)_3$, and $Fe(OTf)_3$ is very particularly preferred.

In one particularly preferred configuration of the present invention, the suitable acids are selected from HCl, $H_2SO_4$, $H_3PO_4$, methanesulfonic acid, trifluoromethanesulfonic acid, para-toluenesulfonic acid, acetic acid, propionic acid, trifluoroacetic acid, trichloroacetic acid, $Mg(OTf)_2$, $Zn(OTf)_2$, $Fe(OTf)_3$, $Cu(OTf)_2$, $Sc(OTf)_2$, $BBr_3$, $BCl_3$ and $BF_3*OEt_2$, very particularly preferably from $H_2SO_4$, $H_3PO_4$, methanesulfonic acid, trifluoromethanesulfonic acid, trifluoroacetic acid, trichloroacetic acid, acetic acid, $Sc(OTf)_2$ or $Fe(OTf)_3$, especially preferably from $H_2SO_4$, methanesulfonic acid, trifluoroacetic acid or $Fe(OTf)_3$.

The acids may be used alone or in a combination of two or more acids.

It is preferable according to the invention for the acid to be used as a pure substance or as a solution in a suitable organic solvent which is inert under the reaction conditions, especially in the solvent previously selected for the reaction, preferably at a concentration of >30% by weight, particularly preferably at a concentration of >60% by weight. Suitable organic solvents are especially the solvents preferred for the overall process.

Particular preference is given, however, to using the acid as a pure substance and in the case of mineral acids in their commercially available concentrated form without further dilution.

Preference is given to using the acid in a form not (additionally) diluted with water (with respect to the commercially available form).

According to the invention, the acid is used in a proportion of >0.0001 equivalent and ≤0.3 equivalent, preferably >0.001 equivalent and ≤0.15 equivalent and very particularly preferably >0.005 equivalent and ≤0.05 equivalent, based on the total molar amount of compound (II) used.

The reaction is preferably conducted in a temperature range of −78 to 200° C., particularly preferably at temperatures from −20 to 100° C. and very particularly preferably between 0° C. and 50° C.

The reaction can be carried out at elevated or else reduced pressure. However, it is preferably conducted at standard pressure, e.g. in the range of 1013 hPa 300 hPa, or in the range of 1013 hPa 100 hPa, or in the range of 1013 hPa 50 hPa.

Suitable diluents or solvents for carrying out the processes according to the invention are, in principle, all organic solvents which are inert under the specific reaction conditions. Examples include: halohydrocarbons (e.g. chlorohydrocarbons such as tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), nitriles such as acetonitrile, propionitrile, butyronitrile, isobutyronitrile, benzonitrile, m-chlorobenzonitrile, aliphatic, cycloaliphatic or aromatic hydrocarbons (e.g. pentane, hexane, heptane, octane, nonane and technical grade hydrocarbons, cyclohexane, methylcyclohexane, petroleum ether, ligroin, benzene, toluene, anisole, xylene, mesitylene, nitrobenzene), esters (e.g. methyl acetate, ethyl acetate, isopropyl acetate, butyl acetate, isobutyl acetate, dimethyl carbonate, dibutyl carbonate, ethylene carbonate); amides (e.g. N,N-dimethylformamide (DMF), N,N-dipropylformamide, N,N-dibutylformamide (DBF), N,N-dimethylacetamide (DMAC), N-methylpyrrolidone (NMP), aliphatic or cycloaliphatic ethers (e.g. 1,2-dimethoxyethane (DME), diglyme, tetrahydrofuran (THF), 2-methyl-THF, 1,4-dioxane, methyl tert-butyl ether), carboxylic acids (e.g. acetic acid, n-propanoic acid, n-butanoic acid), ketones (e.g. acetone, ethyl methyl ketone, methyl isobutyl ketone).

Preferred diluents or solvents are aromatic hydrocarbons, especially benzene, toluene, xylene, mesitylene, chlorobenzene or dichlorobenzene; halogenated hydrocarbons, especially dichloromethane, chloroform, 1,2-dichloroethane or carbon tetrachloride; esters, especially ethyl acetate, isopropyl acetate and butyl acetate; amides, especially DMF, DMAC and NMP; nitriles, especially acetonitrile or propionitrile; or carboxylic acids, especially acetic acid or n-propanoic acid.

In one particularly preferred embodiment, the solvent is a nitrile, especially acetonitrile, or a carboxylic acid, especially acetic acid.

The solvents may be used alone or in a combination of two or more.

The duration of the halogenation of the compounds of the formula (II) is short and is preferably in the range from 0.15 h to 5 h, particularly preferably in the range from 0.25 h to 3 h. A longer reaction time is possible but is not expedient from an economic point of view.

According to the invention, the halogenating compound can be added in pure form as a solid or as a suspension or solution to a solution of the compound of the general formula (II).

In one preferred configuration of the process according to the invention, however, a solution of the compound of the general formula (II) is metered into a suspension or solution of the halogenating compound in a solvent or diluent according to the invention.

Preference is given to using the abovementioned solvents or diluents preferred according to the invention.

The duration of the metering can be in a preferred range from 0.5 to 6 hours, particularly preferably from 1 to 4 hours. Longer metering times are also possible from a technical point of view but are not expedient from an economic point of view.

The metering preferably takes place in a temperature range from −78 to 200° C., particularly preferably at temperatures from −20 to 100° C. and very particularly preferably between 0° C. and 50° C. In one advantageous configuration, the temperature at which metering is performed corresponds to the reaction temperature.

In one preferred configuration of the process according to the invention, the compounds of the general formula (II) are reacted in a suitable organic solvent with 1,3-diiodo-5,5-dimethylhydantoin (DIDMH) with addition of 0.2 equivalent of one of the abovementioned preferred acids according to the invention, based on the total molar amount of the compound (II) used, at 1013 hPa 300 hPa and a temperature of −20 to 100° C. to give compounds of the general formula (I). The reaction mixture is stirred for a period of 0.15 to 6 hours under the same conditions. The reaction time is preferably selected such that the reaction is ended with complete conversion ascertained by means of HPLC[a].

In one particularly preferred configuration of the process according to the invention, the compounds of the general formula (II) are metered, together with 0.05 equivalent of sulfuric acid, based on the total molar amount of the compound (II) used, as a solution in acetonitrile into a suspension of 1,3-diiodo-5,5-dimethylhydantoin (DIDMH) in acetonitrile at 1013 hPa 50 hPa and a temperature of 0 to 50° C. between 0.25 and 3 h. The reaction mixture is stirred for a period of 0.25 to 6 hours under the same conditions. The reaction time is preferably selected such that the reaction is ended with complete conversion ascertained by means of HPLC[a].

In the process according to the invention, the compounds of the formula (I) are preferably isolated and worked up following the reaction.

To isolate and work up the halopyrazoles of the general formula (I), excess halogenating agent can be rendered harmless by adding suitable reducing agents known to those skilled in the art (for example sodium sulfite or sodium thiosulfate). The reducing agent may be added in pure form as a solid or as a saturated aqueous solution. The product, directly or after partial removal of the solvent, for example after removal of 50% of the solvent, may be precipitated out by diluting the reaction mixture with water and isolated by filtration. As an alternative, the product may be extracted into an organic solvent and isolated after aqueous work-up and subsequent removal of the solvent or extractant.

EXAMPLES

The following examples explain the process according to the invention in more detail without limiting the invention thereto.

1) 1-[2,6-dichloro-4-(1,1,1,2,3,3,3-heptafluoropropan-2-yl)phenyl]-4-iodo-1H-pyrazole (I-1

11.1 g (28.0 mmol, 0.5 eq) of 1,3-diiodo-5,5-dimethylhydantoin were initially charged in 25 ml of acetonitrile and admixed over 0.5 h at an internal temperature of 20° C. with a solution of 22.7 g (purity: 93%, 55.6 mmol, 1.0 eq) of 1-[2,6-dichloro-4-[1,2,2,2-tetrafluoro-1-(trifluoromethyl) ethyl]phenyl]pyrazole and 0.28 g (2.8 mmol, 0.05 eq) of 96% sulfuric acid, dissolved in 25 ml of acetonitrile. After addition was complete, the mixture was stirred further for 10 min and subsequently complete conversion to the iodopyrazole was detected by means of HPLC[a]. 10 ml of water were then added and the reaction was terminated by adding 5 ml of saturated sodium sulfite solution. The solvent was partially distilled off under reduced pressure and the product was filtered after precipitation with 20 ml of water. The residue was washed twice with 80 ml each time of water and, after drying under reduced pressure at 40° C., the product was obtained as a colourless-to-yellowish solid: yield 29.1 g (98% of theory).

$^1$H-NMR (CDCl$_3$, 400 MHz) δ (ppm)=7.84 ppm (s, 1H); 7.71 ppm (s, 2H); 7.65 ppm (s, 1H).

2) 1-[2,6-dichloro-4-(1,1,1,2,3,3,3-heptafluoropropan-2-yl)phenyl]-4-iodo-1H-pyrazole (I-1

5.1 g (12.9 mmol, 0.505 eq) of 1,3-diiodo-5,5-dimethylhydantoin were initially charged in 10 ml of acetonitrile and admixed over 15 min at an internal temperature of 20° C. with a solution of 10.0 g (purity: 98%, 25.7 mmol, 1.0 eq) of 1-[2,6-dichloro-4-[1,2,2,2-tetrafluoro-1-(trifluoromethyl) ethyl]phenyl]pyrazole and 80 mg (1.3 mmol, 0.05 eq) of glacial acetic acid, dissolved in 10 ml of acetonitrile. After addition was complete, the reaction was heated to 50° C. and stirred further at this temperature. After 10 h, a 90% conversion to the iodopyrazole was detectable by means of HPLC[a]. The reaction was terminated by adding 5 ml of saturated sodium sulfite solution and the product was filtered after precipitation with 100 ml of water. The residue was washed twice with 20 ml each time of water and, after drying under reduced pressure at 40° C., the product was obtained as a pale orange solid: yield 12.1 g (82% of theory).

3) 1-[2,6-dichloro-4-(1,1,1,2,3,3,3-heptafluoropropan-2-yl)phenyl]-4-iodo-1H-pyrazole (I-1

51.4 g (129.9 mmol, 0.505 eq) of 1,3-diiodo-5,5-dimethylhydantoin were initially charged in 100 ml of acetonitrile and admixed over 0.5 h at an internal temperature of 20° C. with a solution of 100.0 g (purity: 98%, 257.2 mmol, 1.0 eq) of 1-[2,6-dichloro-4-[1,2,2,2-tetrafluoro-1-(trifluoromethyl) ethyl]phenyl]pyrazole and 26 mg (0.26 mmol, 0.001 eq) of 96% sulfuric acid, dissolved in 100 ml of acetonitrile. After addition was complete, the reaction mixture was stirred at 50° C. After 1 h, complete conversion to the iodopyrazole was detectable by means of HPLC[a]. 50 ml of water were then added and the reaction was terminated by adding 50 ml of saturated sodium sulfite solution. The solvent was partially distilled off under reduced pressure and the product was filtered after precipitation with 300 ml of water. The residue was washed twice with 100 ml each time of water and, after drying under reduced pressure at 40° C., the product was obtained as a colourless-to-yellowish solid: yield 129.5 g (94% of theory).

4) 1-[2,6-dichloro-4-(1,1,1,2,3,3,3-heptafluoropropan-2-yl)phenyl]-4-iodo-1H-pyrazole (I-1

5.1 g (12.9 mmol, 0.505 eq) of 1,3-diiodo-5,5-dimethylhydantoin were initially charged in 10 ml of acetonitrile and admixed over 15 min at an internal temperature of 20° C. with a solution of 10.0 g (purity: 98%, 25.7 mmol, 1.0eq) of 1-[2,6-dichloro-4-[1,2,2,2-tetrafluoro-1-(trifluoromethyl)ethyl]phenyl]pyrazole and 134 mg (0.26 mmol, 0.01 eq) of Fe(OTf)$_3$, dissolved in 10 ml of acetonitrile. After addition was complete, the reaction mixture was stirred further at RT. After 2 h, complete conversion to the iodopyrazole was detectable by means of HPLC[a]. The reaction was then terminated by adding 5 ml of saturated sodium sulfite solution and the product was filtered after precipitation with 100 ml of water. The residue was washed twice with 100 ml each time of water and, after drying under reduced pressure at 40° C., the product was obtained as a colourless-to-yellowish solid: yield 12.7 g (88% of theory).

5) 1-[2,6-dichloro-4-(1,1,1,2,3,3,3-heptafluoropropan-2-yl)phenyl]-4-iodo-1H-pyrazole (I-1

6.3 g (27.0 mmol, 1.05 eq) of N-iodosuccinimide were initially charged in 10 ml of acetonitrile and admixed over 15 min at an internal temperature of 20° C. with a solution of 10.0 g (purity: 98%, 25.7 mmol, 1.0 eq) of 1-[2,6-dichloro-4-[1,2,2,2-tetrafluoro-1-(trifluoromethyl)ethyl]phenyl]pyrazole and 131 mg (1.29 mmol, 0.05 eq) of 96% sulfuric acid, dissolved in 10 ml of acetonitrile. After addition was complete, the reaction mixture was stirred at this temperature. After 1 h, complete conversion to the iodopyrazole was detectable by means of HPLC[a]. The reaction was then terminated by adding 5 ml of saturated sodium sulfite solution and the product was filtered after precipitation with 100 ml of water. The residue was washed twice with 100 ml each time of water and, after drying under reduced pressure at 40° C., the product was obtained as a colourless-to-yellowish solid: yield 12.7 g (94% of theory).

6) 1-[2,6-dichloro-4-(1,1,1,2,3,3,3-heptafluoropropan-2-yl)phenyl]-4-iodo-1H-pyrazole (I-1

10.0 g (purity: 97.4%, 25.5 mmol, 1.0eq) of 1-[2,6-dichloro-4-[1,2,2,2-tetrafluoro-1-(trifluoromethyl)ethyl]phenyl]pyrazole were dissolved in 20 ml of acetonitrile and admixed with 0.26 mg (2.55 µmol, 0.0001 eq) of 96% H$_2$SO$_4$. After addition of 1.53 g (3.9 mmol, 0.15 eq) of 1,3-diiodo-5,5-dimethylhydantoin, the solution was heated to 60° C. and stirred at this temperature. After 5 h, a further 1.53 g (3.9 mmol, 0.15 eq) of 1,3-diiodo-5,5-dimethylhydantoin were added and the mixture was stirred further at 60° C., and the addition was repeated after a total of 10 h with a further 2.04 g (5.2 mmol, 0.20 eq) of 1,3-diiodo-5,5-dimethylhydantoin. After a total of 17 h at 60° C., 99% conversion to the iodopyrazole was detectable by means of HPLC[a]. The product was not isolated.

7) 4-bromo-1-[2,6-dichloro-4-(1,1,1,2,3,3,3-heptafluoropropan-2-yl)phenyl]-1H-pyrazole (I-2

3.86 g (13.2 mmol, 0.51 eq) of 1,3-dibromo-5,5-dimethylhydantoin were initially charged in 50 ml of acetonitrile and admixed over 0.5 h at an internal temperature of 20° C. with a solution of 10.0 g (purity: 99%, 26.2 mmol, 1.0eq) of 1-[2,6-dichloro-4-[1,2,2,2-tetrafluoro-1-(trifluoromethyl)ethyl]phenyl]pyrazole and 0.13 g (1.3 mmol, 0.05 eq) of 96% sulfuric acid, dissolved in 50 ml of acetonitrile. After addition was complete, the mixture was stirred further for 10 min and subsequently complete conversion to the bromopyrazole was detected by means of HPLC[a]. 10 ml of water were then added and the reaction was terminated by adding 5 ml of saturated sodium sulfite solution. The solvent was partially distilled off under reduced pressure and the product was filtered after precipitation with 20 ml of water. The residue was washed twice with 80 ml each time of water and, after drying under reduced pressure at 40° C., the product was obtained as a colourless solid: yield 11.6 g (96% of theory).

$^1$H-NMR (CDCl$_3$, 400 MHz): δ (ppm)=7.80 ppm (s, 1H); 7.71 ppm (s, 2H); 7.63 ppm (s, 1H)

8) 4-bromo-1-[2,6-dichloro-4-(1,1,1,2,3,3,3-heptafluoropropan-2-yl)phenyl]-1H-pyrazole (I-2

4.81 g (27.2 mmol, 1.05 eq) of N-bromosuccinimide were initially charged in 10 ml of acetonitrile and admixed over 15 min at an internal temperature of 20° C. with a solution of 10.0 g (purity: 99%, 26.2 mmol, 1.0eq) of 1-[2,6-dichloro-4-[1,2,2,2-tetrafluoro-1-(trifluoromethyl)ethyl]phenyl]pyrazole and 0.13 g (1.3 mmol, 0.05 eq) of 96% sulfuric acid, dissolved in 10 ml of acetonitrile. After addition was complete, the mixture was stirred further at this temperature and, after 1 h, complete conversion to the bromopyrazole was detected by means of HPLC[a]. The reaction was then terminated by adding 5 ml of saturated sodium sulfite solution and the product was filtered after precipitation with 100 ml of water. The residue was washed twice with 20 ml each time of water and, after drying under reduced pressure at 40° C., the product was obtained as a colourless solid: yield 11.8 g (96% of theory).

9) 4-bromo-1-[2,6-dichloro-4-(1,1,1,2,3,3,3-heptafluoropropan-2-yl)phenyl]-1H-pyrazole (I-2

2.0 g (7.1 mmol, 0.55 eq) of dibromoisocyanuric acid were initially charged in 10 ml of acetonitrile and admixed at an internal temperature of 20° C. with 5.0 g (purity: 98%, 12.9 mmol, 1.0 eq) of 1-[2,6-dichloro-4-[1,2,2,2-tetrafluoro-1-(trifluoromethyl)ethyl]phenyl]pyrazole and 63 mg (0.6 mmol, 0.05 eq) of 96% sulfuric acid. After addition was complete, the mixture was stirred further at this temperature and, after 30 min, complete conversion to the bromopyrazole was detected by means of HPLC[a]. The reaction was then terminated by adding 5 ml of saturated sodium sulfite solution and the isocyanuric acid formed was removed by filtration after dilution with 20 ml of acetonitrile. The mother liquor was admixed dropwise with 150 ml of water and the precipitated solid was filtered. The residue was washed twice with 30 ml each time of water and, after drying under reduced pressure at 40° C., the product was obtained as a colourless solid: yield 5.8 g (95% of theory).

Further Experiments with Respect to the Acids:

Table 1) gives an overview of further experiments that were carried out analogously to experiment 1) and the conversions of compound (1-1) achieved, determined by means of HPLC[a].

There was variation of the acid used, the temperature and the reaction time. All other parameters and reactants were kept the same.

TABLE 1

| Acid | Temperature (° C.) | Time (h) | Conversion (%) |
|---|---|---|---|
| HCl (37%) | 40 | 24 | 85 |
| $H_3PO_4$ | 40 | 11 | 89 |
| trifluoroacetic acid | 40 | 9 | 91 |
| para-toluenesulfonic acid | 25 | 1 | 88 |
| $Mg(OTf)_2$ | 40 | 6.5 | 91 |
| $Ca(OTf)_2$ | 40 | 6.5 | 91 |
| methanesulfonic acid | 25 | 2 | 90 |
| $Fe_2(NO_3)_3 * 9H_2O$ | 40 | 2 | 91 |
| $Mg(NO_3)_2 * 6H_2O$ | 40 | 7 | 88 |
| $BF_3 * EtO_2$ | 25 | 3 | 92 |
| $MgSO_4 * 4H_2O$ | 40 | 12 | 60 |

Comparative Example without Addition of Acid:

1-[2,6-dichloro-4-(1,1,1,2,3,3,3-heptafluoropropan-2-yl)phenyl]-4-iodo-1H-pyrazole (I-1

0.5 g (1.3 mmol, 1.0 eq) of 1-[2,6-dichloro-4-[1,2,2,2-tetrafluoro-1-(trifluoromethyl)ethyl]phenyl]pyrazole were initially charged in 10 ml of acetonitrile and admixed with 2.85 g (0.7 mmol, 0.55 eq) of 1,3-diiodo-5,5-dimethylhydantoin. The reaction mixture was heated to 65-70° C. and stirred at this temperature for 15 h. After this time, 54% conversion to the desired iodinated product was detectable by means of $HPLC^{a)}$. The product was not isolated.

The following halogenated N-arylpyrazoles of the general formula (I) were preparable analogously to experiments 1) and 7):

4-bromo-1-[2-bromo-4-(1,1,1,2,3,3,3-heptafluoropropan-2-yl)-6-(trifluoromethoxy)phenyl]-1H-pyrazole (I-3

Conversion by $HPLC^{a)}$: >99% (r.t., 1 h)
$^1$H-NMR ($CDCl_3$, 400 MHz) δ (ppm)=7.92 (d, J 1.9 Hz, 1H), 7.79 (s, 1H), 7.63 (s, 2H).

4-bromo-1-[2-chloro-4-(1,1,1,2,3,3,3-heptafluoropropan-2-yl)-6-(trifluoromethoxy)phenyl]-1H-pyrazole (I-4

Conversion by $HPLC^{a)}$: >99% (r.t., 1 h)
$^1$H-NMR ($CDCl_3$, 400 MHz) δ (ppm)=7.80 (d, J 1.8 Hz, 1H), 7.79 (s, 1H), 7.64 (s, 1H), 7.59 (s, 1H).

4-bromo-1-[2-chloro-4-[1,2,2,2-tetrafluoro-1-(trifluoromethyl)ethyl]-6-(trifluoromethyl)phenyl]-1H-pyrazole (I-5

Conversion by $HPLC^{a)}$: >99% (r.t., 1 h)
$^1$H-NMR (DMSO-$d_6$, 400 MHz) δ (ppm)=8.48 (br s, 1H), 8.47 (s, 1H), 8.06 (br s, 1H), 8.03 (s, 1H).

4-bromo-1-[2-bromo-4-[1,2,2,2-tetrafluoro-1-(trifluoromethyl)ethyl]-6-(trifluoromethyl)phenyl]-1H-pyrazole (I-6

Conversion by $HPLC^{a)}$: >99% (r.t., 4 h)
$^1$H-NMR ($CDCl_3$, 400 MHz) δ (ppm)=8.17 (br s, 1H), 7.99 (br s, 1H), 7.79 (s, 1H), 7.62 (s, 1H).

4-bromo-1-[2-methyl-4-[1,2,2,2-tetrafluoro-1-(trifluoromethyl)ethyl]-6-(trifluoromethyl)phenyl]-1H-pyrazole (I-7

Conversion by $HPLC^{a)}$: >99% (40° C., 1 h)
$^1$H-NMR ($CDCl_3$, 400 MHz) δ (ppm)=7.87 (br s, 1H), 7.78 (br s, 1H), 7.7 (s, 1H), 7.59 (s, 1H), 2.13 (s, 3H).

1-[2-bromo-4-(1,1,1,2,3,3,3-heptafluoropropan-2-yl)-6-(trifluoromethoxy)phenyl]-4-iodo-1H-pyrazole (I-8

Conversion by $HPLC^{a)}$: >99% (r.t., 0.5 h)
$^1$H-NMR ($CDCl_3$, 400 MHz) δ (ppm)=7.92 (d, J 1.8 Hz, 1H), 7.83 (s, 1H), 7.65 (s, 1H), 7.63 (s, 1H).

1-[2-chloro-4-(1,1,1,2,3,3,3-heptafluoropropan-2-yl)-6-(trifluoromethoxy)phenyl]-4-iodo-1H-pyrazole (I-9

Conversion by $HPLC^{a)}$: >99% (r.t., 0.5 h)
$^1$H-NMR ($CDCl_3$, 400 MHz) δ (ppm)=7.83 (d, J 1.9 Hz, 1H), 7.77 (s, 1H), 7.66 (s, 1H), 7.59 (s, 1H).

1-[2-chloro-4-[1,2,2,2-tetrafluoro-1-(trifluoromethyl)ethyl]-6-(trifluoromethyl)phenyl]-4-iodo-1H-pyrazole (I-10

Conversion by $HPLC^{a)}$: >99% (r.t., 0.5 h)
$^1$H-NMR (DMSO-$d_6$, 400 MHz) δ (ppm)=8.47 (br s, 1H), 8.38 (s, 1H), 8.05 (br s, 1H), 7.97 (s, 1H).

1-[2-bromo-4-[1,2,2,2-tetrafluoro-1-(trifluoromethyl)ethyl]-6-(trifluoromethyl)phenyl]-4-iodo-1H-pyrazole (I-11

Conversion by $HPLC^{a)}$: >99% (r.t., 0.5 h)
$^1$H-NMR ($CDCl_3$, 400 MHz) δ (ppm)=8.16 (br s, 1H), 7.99 (br s, 1H), 7.83 (s, 1H), 7.64 (s, 1H).

4-iodo-1-[2-methyl-4-[1,2,2,2-tetrafluoro-1-(trifluoromethyl)ethyl]-6-(trifluoromethyl)phenyl]-1H-pyrazole (I-12

Conversion by $HPLC^{a)}$: >99% (r.t., 0.5 h)
$^1$H-NMR ($CDCl_3$, 400 MHz) δ (ppm)=7.87 (br s, 1H), 7.81 (s, 1H), 7.78 (br s, 1H), 7.61 (s, 1H), 2.11 (s, 3H).

Methods:

The NMR data of the examples are listed in conventional form (δ values, multiplet splitting, number of hydrogen atoms).

The solvent and the frequency in which the NMR spectrum was recorded are stated in each case.

[a)] HPLC (High Performance Liquid Chromatography) on a reversed-phase column (C18), Agilent 1100 LC system; Phenomenex Prodigy 100×4 mm ODS3; eluent A: acetonitrile (0.25 ml/l); eluent B: water (0.25 ml TFA/l); linear gradient from 5% acetonitrile to 95% acetonitrile in 7.00 min, then 95% acetonitrile for a further 1.00 min; oven temperature 40° C.; flow rate: 2.0 ml/min.

The invention claimed is:
1. A process for preparing a compound of formula (I)

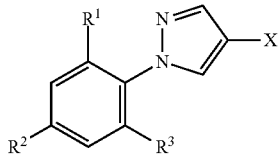

wherein
X is chlorine, bromine or iodine;
$R^1$ is hydrogen, cyano, halogen, $C_1$-$C_4$-alkyl optionally substituted by halogen or CN, or $C_1$-$C_4$-alkoxy optionally substituted by halogen,
$R^2$ is trifluoromethylsulfonyl, trifluoromethylsulfinyl, trifluoromethylsulfanyl, halogen, $C_1$-$C_4$-alkyl optionally substituted by halogen, or $C_1$-$C_4$-alkoxy optionally substituted by halogen; and
$R^3$ is hydrogen, cyano, halogen, $C_1$-$C_4$-alkyl optionally substituted by halogen or CN, or $C_1$-$C_4$-alkoxy optionally substituted by halogen,
comprising halogenating a compound of formula (II)

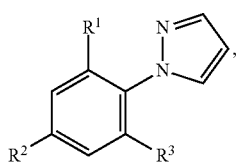

wherein $R^1$, $R^2$ and $R^3$ are as defined above,
with an organic halogenating compound with addition of ≥0.0001 equivalent and <0.3 equivalent, based on the total molar amount of compound of the formula (II) used, of at least one acid selected from the group consisting of mineral acids, sulfonic acids, carboxylic acids and Lewis acids.

2. The process according to claim 1, wherein the organic halogenating compound is selected from the N-halosuccinimides, the 1,3-dihalo-5,5-dimethylhydantoins or the halocyanuric acids.

3. The process according to claim 1, wherein the halogenating compound is selected from N-bromosuccinimide (NBS), N-iodosuccinimide (NIS), 1,3-dibromo-5,5-dimethylhydantoin (DBDMH), 1,3-diiodo-5,5-dimethylhydantoin (DIDMH), 1,3,5-tribromo-1,3,5-triazine-2,4,6-trione or 1,3-dibromo-1,3,5-triazine-2,4,6-trione.

4. The process according to claim 1, wherein the acid is used in a proportion of ≥0.001 equivalent and ≤0.15 equivalent, based on the total molar amount of compound (II) used.

5. The process according to claim 1, wherein the at least one acid is a carboxylic acid.

6. The process according to claim 1, wherein the acid is selected from HF, HCl, HBr, HI, $H_2SO_4$, $HNO_3$ and $H_3PO_4$, optionally substituted arylsulfonic and alkylsulfonic acids, optionally substituted alkylcarboxylic and arylcarboxylic acids, optionally substituted alkyldicarboxylic and aryldicarboxylic acids, and anhydrous or hydrated fluoride, chloride or bromide salts, nitrates, acetates, sulfates or trifluoromethanesulfonates (OTf) of lithium or of the alkaline earth metals, of the boron-group metals and of the transition metals.

7. The process according to claim 1, wherein the acid is selected from HCl, HF, $HNO_3$, $H_2SO_4$, $H_3PO_4$, methanesulfonic acid, trifluoromethanesulfonic acid, benzenesulfonic acid, para-toluenesulfonic acid, acetic acid, propionic acid, trifluoroacetic acid, trichloroacetic acid and anhydrous or hydrated salts selected from the fluoride, chloride or bromide salts, nitrates or trifluoromethanesulfonates (OTf) of the metals B or Al, from the nitrates or trifluoromethanesulfonates (OTf) of the alkaline earth metals Mg or Ca, or the nitrates or trifluoromethanesulfonates (OTf) of the transition metals Fe, Zn, Cu or Sc.

8. The process according to claim 1, wherein the acid is selected from the group consisting of $HNO_3$, HF, $H_2SO_4$, methanesulfonic acid, para-toluenesulfonic acid, acetic acid, trifluoroacetic acid, trichloroacetic acid, $Mg(NO_3)_2$, $Ca(NO_3)_2$, $Fe_2(NO_3)_3$, $Zn(NO_3)_2$, $Zn(OTf)_2$, $Cu(NO_3)_2$, $Sc(NO_3)_3$, $Ca(OTf)_2$, $Mg(OTf)_2$, $Cu(OTf)_2$, $BBr_3$, $BCl_3$, $BF_3*OEt_2$, $Al(NO_3)_3$, $Al(OTf)_3$, $Fe(OTf)_3$, $Cu(OTf)_2$ and $Sc(OTf)_3$.

9. The process according to claim 1, wherein the reaction is conducted in a temperature range of −78 to 200° C.

10. The process according to claim 1, wherein $R^2$ is halogen-substituted $C_1$-$C_4$-alkyl or halogen-substituted $C_1$-$C_4$-alkoxy.

11. The process according to claim 1, wherein $R^2$ is fluorine-substituted $C_1$-$C_4$-alkyl or fluorine-substituted $C_1$-$C_4$-alkoxy.

12. The process according to claim 1, wherein $R^1$ and $R^3$ in each case independently of one another are a substituent selected from hydrogen, Cl, Br, F, $C_1$-$C_3$-alkyl, halogen-substituted $C_1$-$C_3$-alkyl, $C_1$-$C_3$-alkoxy or halogen-substituted $C_1$-$C_3$-alkoxy.

13. The process according to claim 1, wherein $R^1$ and $R^3$ are not simultaneously hydrogen.

14. The process according to claim 1, wherein
$R^1$ is halogen or ($C_1$-$C_3$)-alkyl,
$R^2$ is fluorine-substituted $C_1$-$C_4$-alkyl or fluorine-substituted $C_1$-$C_4$-alkoxy, and
$R^3$ is halogen, $C_1$-$C_3$-alkyl or fluorine-substituted $C_1$-$C_3$-alkyl, $C_1$-$C_3$-alkoxy or fluorine-substituted $C_1$-$C_3$-alkoxy.

15. The process according to claim 1,
wherein X is bromine or iodine.

16. The process according to claim 9, wherein
the reaction is conducted in a temperature range from −20 to 100° C.